(12) United States Patent
Terry et al.

(10) Patent No.: US 10,219,748 B2
(45) Date of Patent: Mar. 5, 2019

(54) GASTROINTESTINAL SENSOR IMPLANTATION SYSTEM

(71) Applicant: NUtech Ventures, Lincoln, NE (US)

(72) Inventors: Benjamin Terry, Lincoln, NE (US); Weston Lewis, Williamsburg, VA (US); Wanchuan Xie, Lincoln, NE (US); Pengbo Li, Lincoln, NE (US); Alfred Tsubaki, Omaha, NE (US)

(73) Assignee: NUtech Ventures, Lincoln, NE (US)

( * ) Notice: Subject to any disclaimer, the term of this patent is extended or adjusted under 35 U.S.C. 154(b) by 237 days.

(21) Appl. No.: 15/113,521

(22) PCT Filed: Jan. 21, 2015

(86) PCT No.: PCT/US2015/012209
§ 371 (c)(1),
(2) Date: Jul. 22, 2016

(87) PCT Pub. No.: WO2015/112575
PCT Pub. Date: Jul. 30, 2015

(65) Prior Publication Data
US 2017/0027520 A1    Feb. 2, 2017

Related U.S. Application Data

(60) Provisional application No. 61/930,219, filed on Jan. 22, 2014.

(51) Int. Cl.
*A61B 5/07*     (2006.01)
*A61B 5/00*     (2006.01)
*A61B 1/273*    (2006.01)
*A61B 10/04*    (2006.01)
(Continued)

(52) U.S. Cl.
CPC ............ *A61B 5/6861* (2013.01); *A61B 1/273* (2013.01); *A61B 5/073* (2013.01); *A61B 5/6882* (2013.01);
(Continued)

(58) Field of Classification Search
CPC ...................... A61B 5/6861; A61B 2562/162
See application file for complete search history.

(56) References Cited

U.S. PATENT DOCUMENTS 6,689,056 B1 * 2/2004 Kilcoyne ............ A61B 5/0031
                                            128/898
7,797,033 B2    9/2010 D'andrea et al.
(Continued)

OTHER PUBLICATIONS

International Search Report and Written Opinion for related application No. PCT/US2015/012209, dated Apr. 14, 2015, 13 pages.
(Continued)

*Primary Examiner* — Meredith Weare
(74) *Attorney, Agent, or Firm* — Harness, Dickey & Pierce, P.L.C.

(57) ABSTRACT

A gastrointestinal (GI) sensor deployment device is disclosed. In implementations, the sensor deployment device includes an orally-administrable capsule with a tissue capture device removably coupled to the orally-administrable capsule. The tissue capture device includes a plurality of fasteners for connecting the tissue capture device to GI tissue within a body. A biometric sensor is coupled to the tissue capture device for continuous or periodic monitoring of the GI tract of the body at the GI tissue attachment location. A chamber within the orally-administrable capsule is configured to draw gastrointestinal tissue towards the plurality of fasteners when a fluid pressure of the chamber is increased. An actuator can be configured to cause an increase of the fluid pressure of the chamber. Control circuitry coupled to the actuator can be configured to trigger the actuator to cause the increase of the fluid pressure of the chamber at a selected time.

20 Claims, 16 Drawing Sheets

(51) Int. Cl.
*A61B 10/02* (2006.01)
*A61B 1/04* (2006.01)

(52) U.S. Cl.
CPC ...... *A61B 10/0266* (2013.01); *A61B 10/0283* (2013.01); *A61B 10/04* (2013.01); *A61B 1/041* (2013.01); *A61B 5/4233* (2013.01); *A61B 5/4238* (2013.01); *A61B 5/4255* (2013.01); *A61B 5/6873* (2013.01); *A61B 5/6884* (2013.01); *A61B 5/6885* (2013.01); *A61B 2562/162* (2013.01)

(56) References Cited

U.S. PATENT DOCUMENTS

| | | | |
|---|---|---|---|
| 8,100,920 | B2 | 1/2012 | Gambale et al. |
| 9,668,690 | B1* | 6/2017 | Imran ................ A61N 1/36007 |
| 2006/0167339 | A1* | 7/2006 | Gilad ................. A61B 1/00087 600/101 |
| 2008/0064938 | A1* | 3/2008 | Semler .................. A61B 5/036 600/309 |
| 2011/0319727 | A1 | 12/2011 | Ishihara |
| 2013/0137993 | A1 | 5/2013 | Imran |
| 2014/0187999 | A1* | 7/2014 | Tearney ................ A61B 10/04 600/563 |

OTHER PUBLICATIONS

Menciassi, A. et al., Single and multiple robotic capsules for endoluminal diagnosis and surgery, Biomedical Robotics and Biomechatronics, 2008, 2nd Biennial IEEE RAS & EMBS International Conference on Biomedical Robotics and Biomechatronics, pp. 238-243.

* cited by examiner

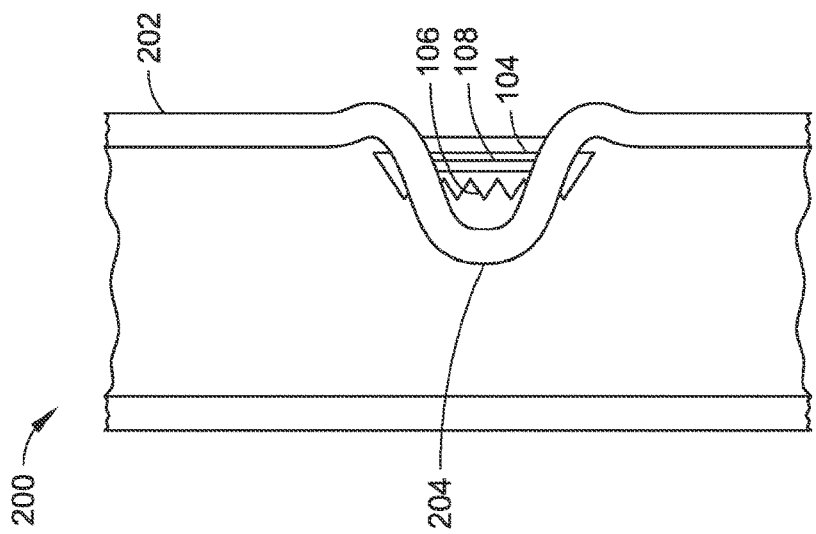
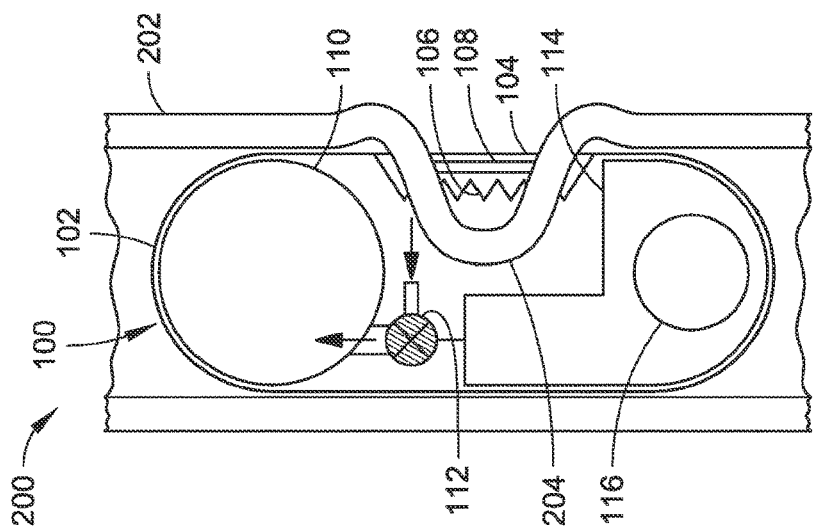
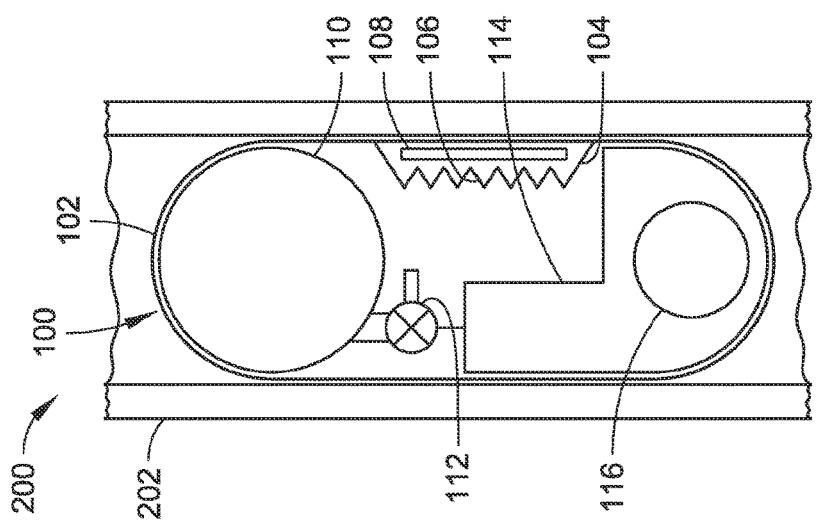

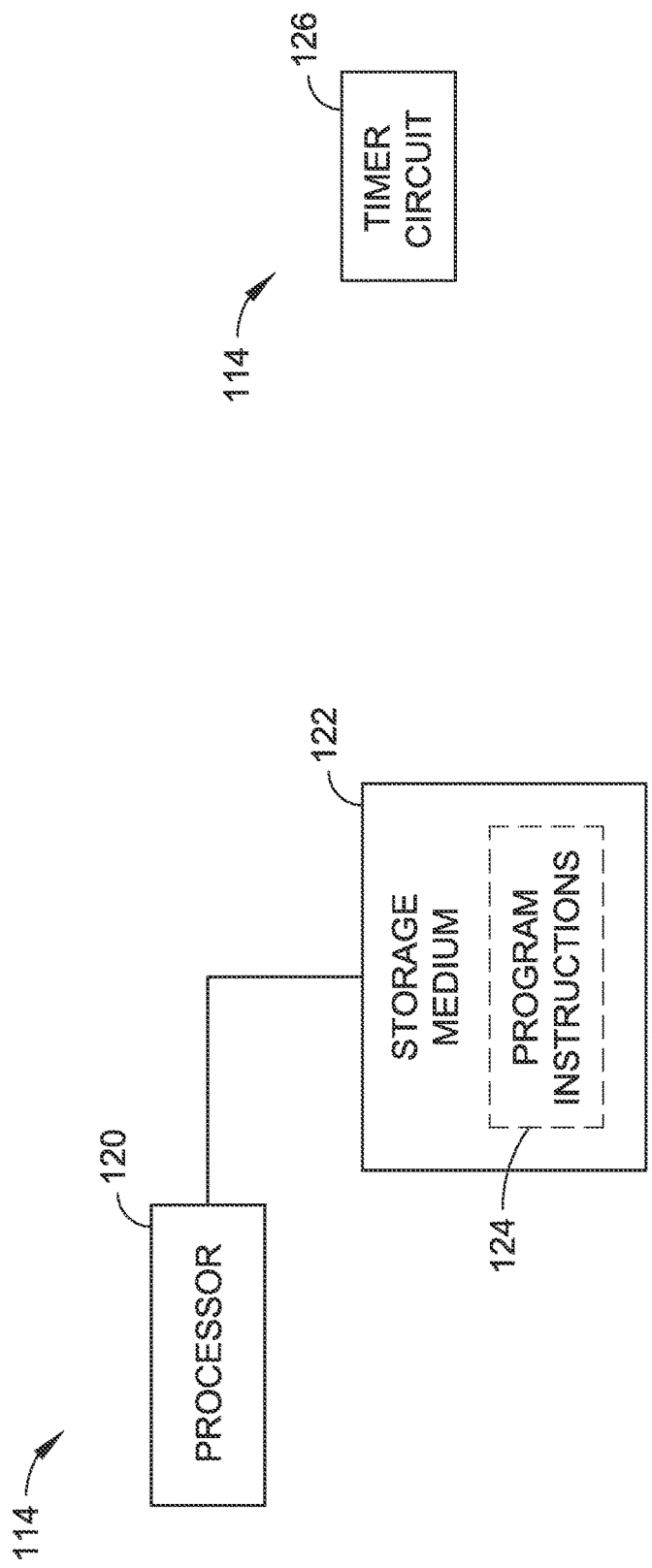

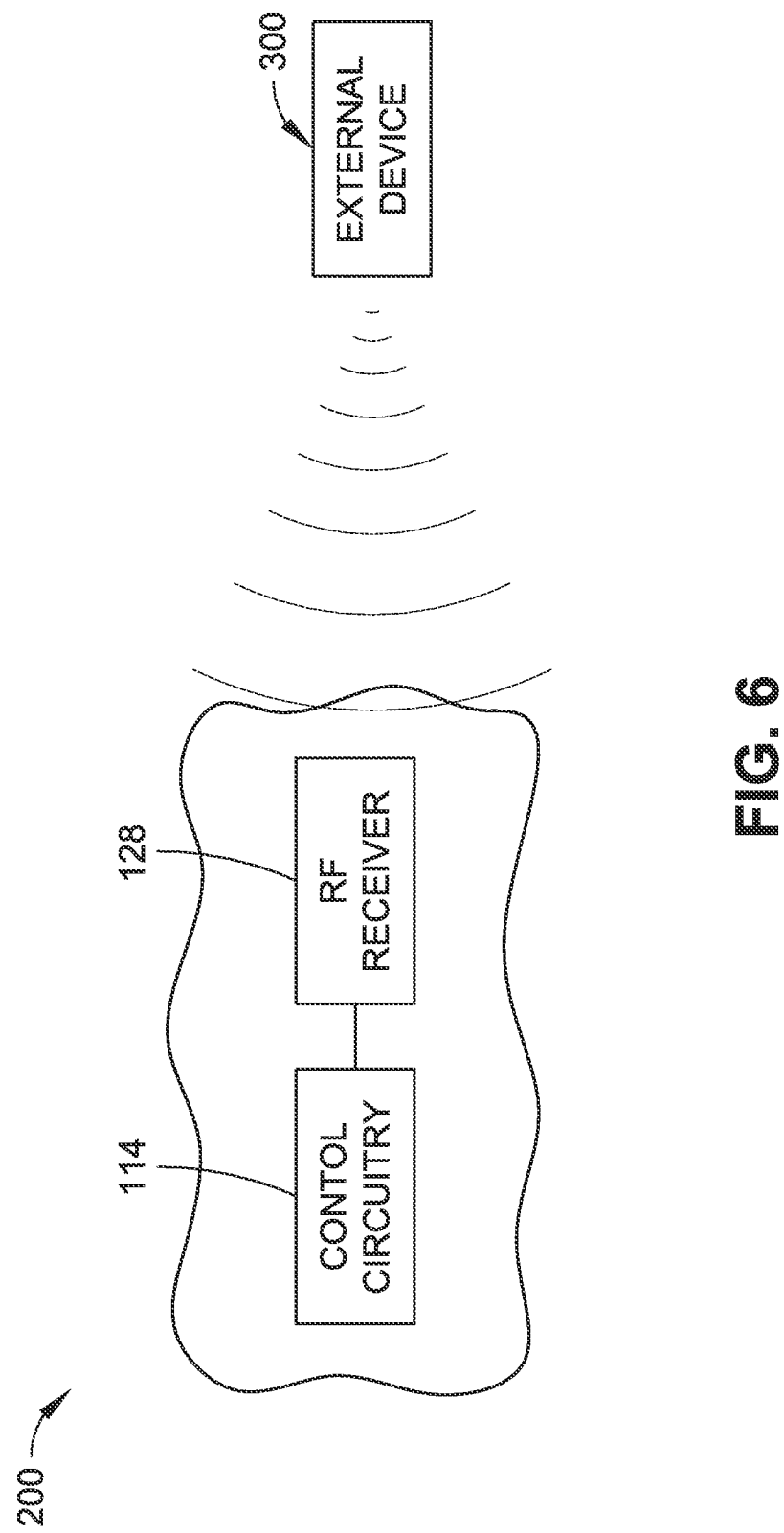

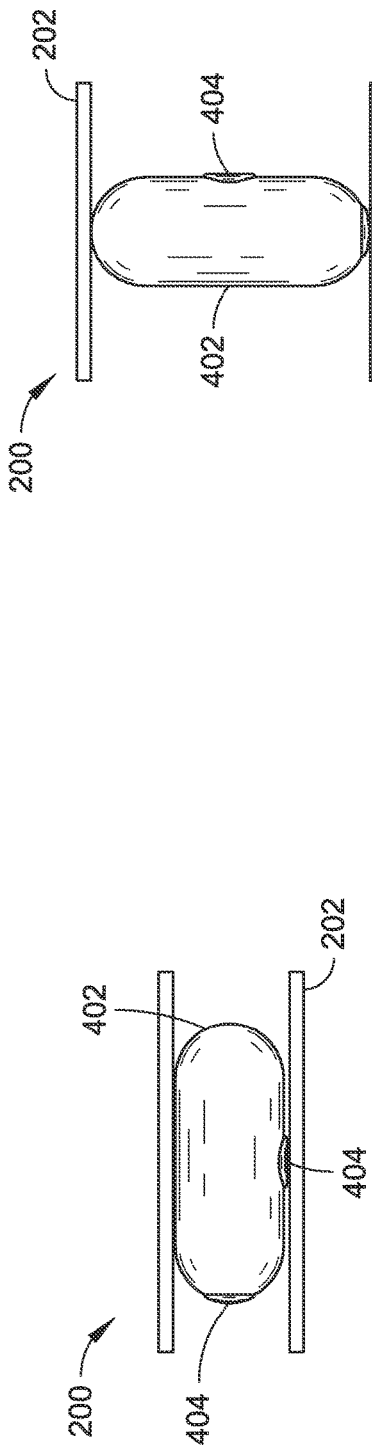
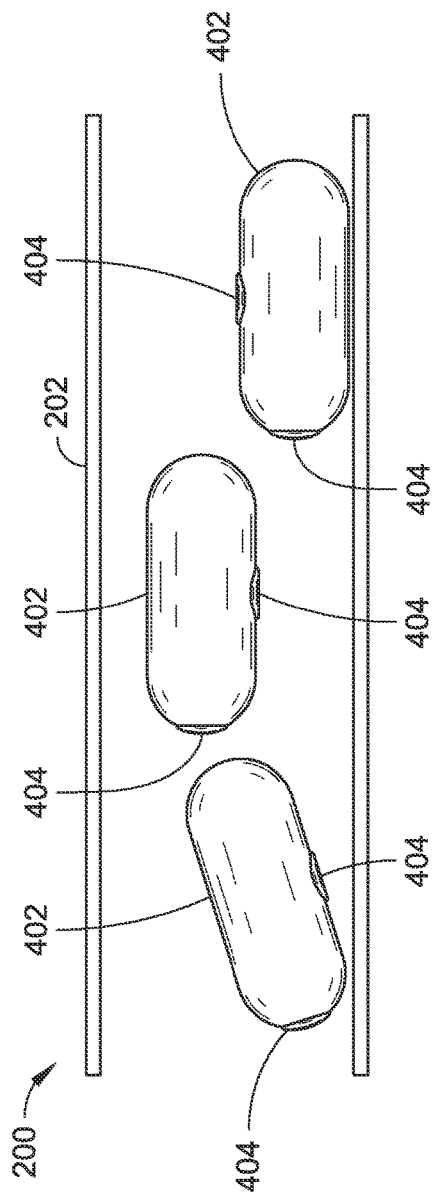
FIG. 13A
FIG. 13B
FIG. 13C

GASTROINTESTINAL SENSOR IMPLANTATION SYSTEM

CROSS-REFERENCE TO RELATED APPLICATIONS

The present application claims the benefit under 35 U.S.C. § 119(e) of U.S. Provisional Application Ser. No. 61/930,219, filed Jan. 22, 2014, and titled "INTUITIVE SENSOR IMPLANTATION SYSTEM," by Benjamin Terry. U.S. Provisional Application Ser. No. 61/930,219 is incorporated herein by reference in its entirety.

GOVERNMENT SUPPORT

This invention was made with U.S. government support under Grant No. NNX10AN62H awarded by the National Aeronautics and Space Administration (NASA). The U.S. government has certain rights in this invention.

BACKGROUND

A capsule endoscope (CE) is one of the most common non-invasive clinical tools in the evaluation of gastrointestinal (GI) tract disease. Currently millions of CEs have been used worldwide to diagnose the small-bowel and to assess GI tract performance. Specifically, CE intervention has been adopted when gastroesophageal reflux disease, obscure gastrointestinal bleeding, Crohn's disease, and polyposis syndromes are indicated. Numerous clinical records and multiple studies have proven that CE intervention is superior to radiologic interventions and push endoscopy because it is non-invasive, has relatively small dimensions, features high image quality, and provides direct visualization of the tissue. Researchers have been looking to expand this method into new domains due to increases in chronic diseases and an aging population.

In the past, the movement of the CE through the GI tract was accepted as being passive and a function of intestine peristalsis. However, in order to complete more accurate diagnostics and treatment of chronic diseases, it is desirable for CEs to offer controllable locomotion, long-term (multi-week) data collection, and drug delivery function. A variety of locomotion systems for CEs have been developed by different methods such as shape memory alloy legs, magnetic drive, and earthworm-like locomotive mechanisms. The CE's capability to acquire long-term physiological indexes is still limited, however, because of its inability to remain in-vivo long-term attachment. The gastrointestinal wall is irregular, slippery, chemically corrosive, and physiologically active due to peristalsis. No traditional technologies enable effective adhesion to such a surface for a prolonged period of time without causing damage or bleeding, and premature loss of the capsule during sensing periods has often been reported. Mucosal adhesive patches may be a potential solution for the long-term attachment requirement, as studied by several research groups. Research groups have shown that high static friction could be created between a colonoscopic device and the GI wall due to mucoadhesion. Mucoadhesive patches have been tested and assembled with a release mechanism in the CEs. Additionally, it has been shown that with 5N preload force, 110 min stable anchoring could be achieved for a 10 mm diameter mucoadhesive patch. These improvements are incremental, however, and still do not enable multi-day or weeks long attachment.

Better clinical outcomes could be obtained if physicians could obtain continuous readings of the small intestine from stationary CEs. Also, in addition to data collection and image recording, long-term attachment may provide other possible functions to CE such as tissue manipulation and drug delivery.

Since the introduction of wireless capsule endoscopy (WCE) in 2000, research communities around the world have been developing miniature swallowable devices that have potential to replace invasive diagnostic tools. Since the WCE's first approval by the Food and Drug Administration (FDA) in 2001, capsule technology has evolved to be used by millions and said to be the most effective diagnostic technique in the small bowel, as well as a subject of worldwide research focused on developing noninvasive diagnostic and therapeutic devices. WCEs such as the Pill-Cam® SB3 (Given Imaging Ltd—now Medtronic Inc., Minnesota, USA)), MiroCam™ v2 (IntroMedic Co, Seoul, South Korea) are clinically available and have established WCE as the gold standard in diagnosing illnesses in the small intestine. Technologies such as miniature integrated circuits (IC) and sensors have become readily available, which has opened the door for development of miniature ingestible devices that can replace standard wearable sensors.

Miniaturizing such technologies and maximizing their efficacy in a zero gravity environment will be a critical step in pursuing distant space exploration. For example, with the coming advent of long-distance human space flights, regular monitoring of astronaut health parameters will be critical to achieve successful and safe missions. The twenty-first century has already seen a paradigm shift in medical technology: groups in both academia and industry are focusing research on developing minimally invasive medical devices for diagnostics, biopsy, therapeutics, and surgery. In the 1980's, the National Aeronautics and Space Administration, NASA, took interest in ingestible sensing technologies, a telemetry capsule used for monitoring body core temperature that is now known as the CorTemp® Ingestible Core Body Temperature Sensor (HQ Inc., Florida, USA). The product of a partnership between the Johns Hopkins University, the Goddard Space Flight Center, and licensing of HQ Inc., the sensor was developed to obtain real time body temperature readings of athletes and astronauts for the prevention of heat related illness (www.spinoffinasa.gov). Used in a number of applications ranging from monitoring athlete core temperature during training, to sleep studies, to monitoring John Glenn's temperature during his final days in space, the device is a prime example of the applicability of a swallowable "smart" device. Gant et al. conducted a study in 2006 involving 10 human subjects who performed physical exercise while having ingested the CorTemp® capsule and reported the temperature measurements to be accurate and reliable. Telemetry capsules like the Cor-Temp® have been said to be valid tools for assessment of core body temperature. The success of CorTemp®, a sensor able to gather data for less than 24 hours while passing through digestive system, suggests that a similar, but much longer duration system could be very useful.

In recent years, the primary need for astronaut health monitoring is associated with service on board the International Space Station (ISS). Astronauts in the ISS have access to sensors such as Blood Pressure/Electrocardiographs (BP/ECG), Heart Rate Monitor 2 (HRM2), acoustic dosimeters, Crew Passive Dosimeters (CPD), and a Tissue Equivalent Proportional Counter (TEPC). The HRM2 is a wearable technology consisting of a watch, transmitter, and chest strap. These devices are assigned to each crew member. The devices record heart rate data which eventually becomes available for downlink and can be reviewed by flight surgeons for diagnosis. The CPD is used to measure radiation exposure and is required to be worn by each member of the United States crew, with other countries having their own version of the sensor. Utilizing sensory devices which are worn as straps or carried is not an ideal method of monitoring astronaut safety during long term missions. Such devices may inhibit motion, are uncomfortable to wear, require maintenance, and interfere with daily activities.

SUMMARY

A micro-robotic capsule (MRC) for implantation of a sensor within the gastrointestinal lining of a body is described in this disclosure. A system and method are also described in accordance with various implementations of the MRC. In one implementation, a sensor deployment device is embodied by an MRC including an orally-administrable capsule with a tissue capture device removably coupled to the orally-administrable capsule. The tissue capture device includes a plurality of fasteners (e.g., micro-needles) for connecting the tissue capture device to GI tissue within a body. A biometric sensor is coupled to the tissue capture device for long term (e.g., several days, weeks, or months long) implantation within the GI tract of the body at the attachment site of the tissue capture device. To facilitate the attachment to the GI tissue, a chamber within the orally-administrable capsule is configured to draw the GI tissue towards the plurality of fasteners when a fluid pressure of the chamber is increased. An actuator is configured to cause an increase of the fluid pressure of the chamber when triggered by control circuitry coupled to the actuator. The control circuitry is configured to trigger the actuator at a selected time. For example, the control circuitry can be configured to trigger the actuator at a predetermined time associated with the orally-administrable capsule reaching a particular location within the GI tract, such as the small intestine or a particular portion thereof.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

FIG. 4A is a schematic view of a sensor deployment device within a gastrointestinal lumen of a body, in accordance with an embodiment of the present disclosure.

FIG. 4B is a schematic view of a sensor deployment device within a gastrointestinal lumen of a body, wherein a tissue capture device carried by the sensor deployment device is being connected to gastrointestinal tissue via controlled fluid flow, in accordance with an embodiment of the present disclosure.

FIG. 4C is a schematic view of a tissue capture device connected to gastrointestinal tissue within a gastrointestinal lumen of a body, in accordance with an embodiment of the present disclosure.

FIG. 5A is a schematic view of a control circuit within a sensor deployment device, in accordance with an embodiment of the present disclosure.

FIG. 5B is a schematic view of a control circuit within a sensor deployment device, in accordance with an embodiment of the present disclosure.

FIG. 6 is a schematic view of a control circuit within a sensor deployment device inside a body in wireless communication with a second device external to the body, in accordance with an embodiment of the present disclosure.

Figure 9B:
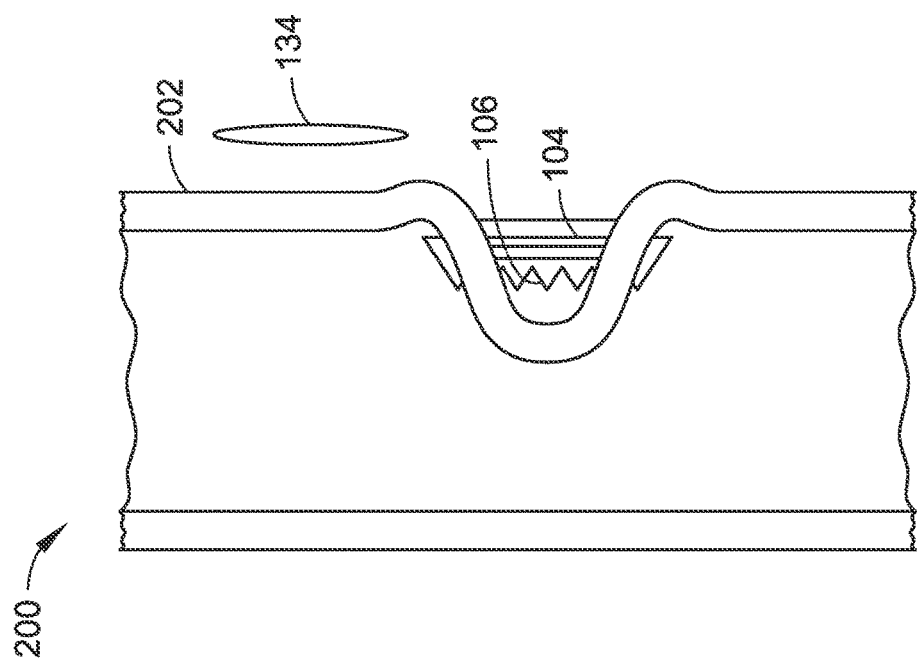
Figure 9A:
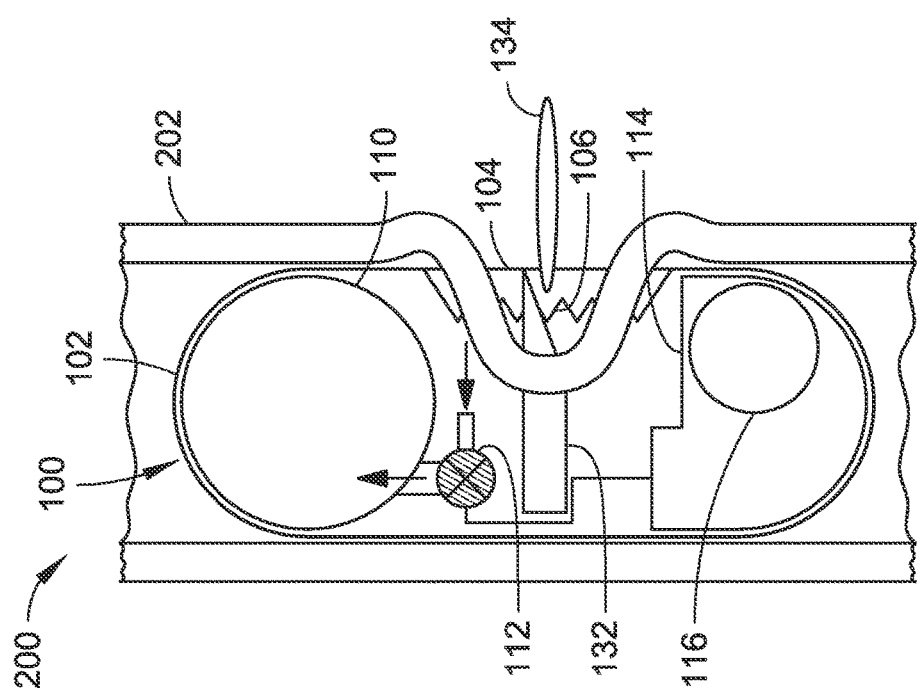

FIG. 9A is a schematic view of an orally-administrable deployment device for implanting sustained release drugs (SRDs) in the intraperitoneal space, wherein a tissue capture device carried by the deployment device is being connected to gastrointestinal tissue via controlled fluid flow, and wherein and SRD is deployed into the intraperitoneal space via an opening within the tissue capture device, in accordance with an embodiment of the present disclosure.

FIG. 9B is a schematic view of a tissue capture device connected to gastrointestinal tissue within a gastrointestinal lumen of a body, wherein the tissue capture device reseals an incision made in the gastrointestinal tissue for deployment of an SRD within the intraperitoneal space, in accordance with an embodiment of the present disclosure.

Figure 10:
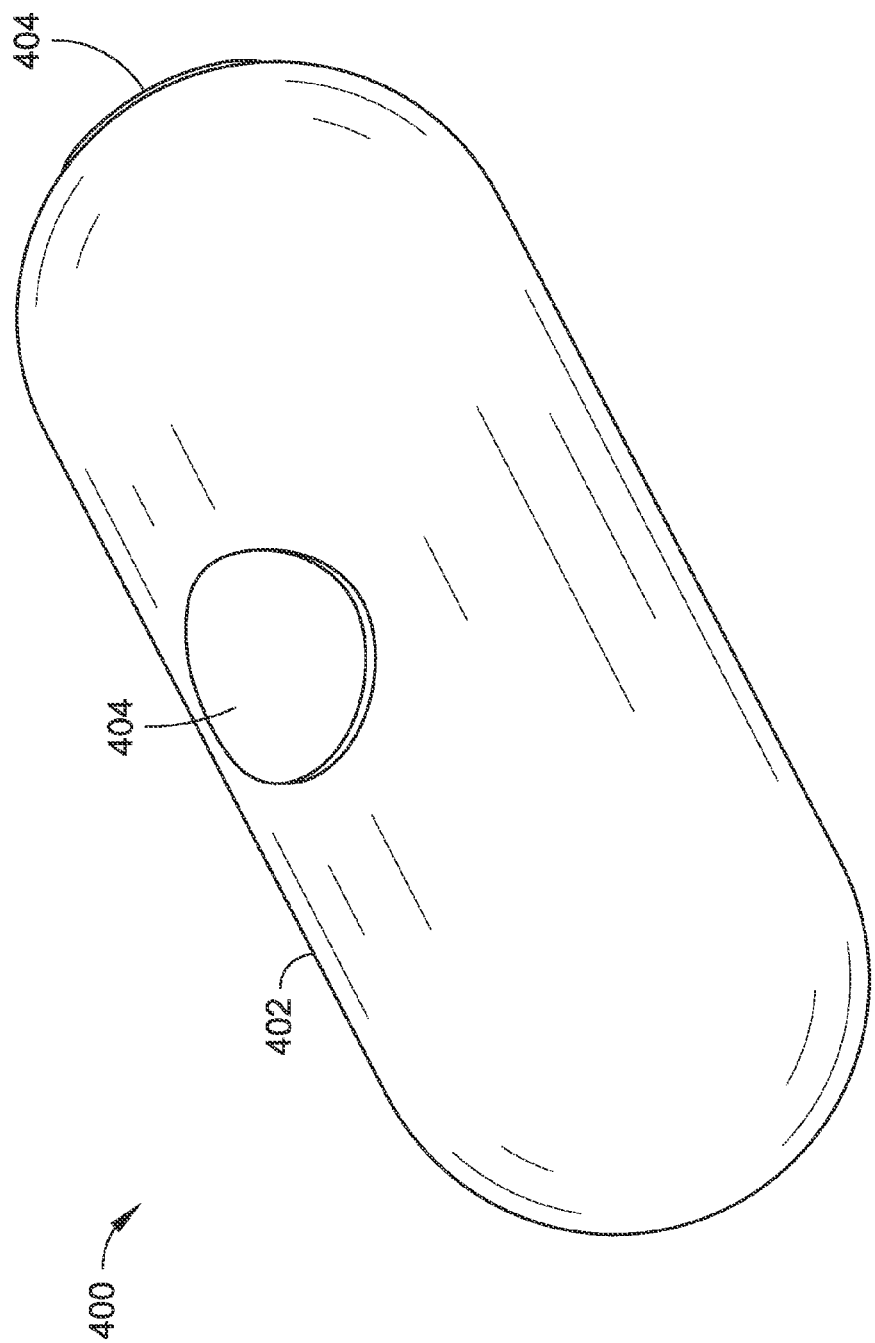

FIG. 10 is a schematic view of a gastrointestinal pressure sensing device, in accordance with an embodiment of the present disclosure.

Figure 11:
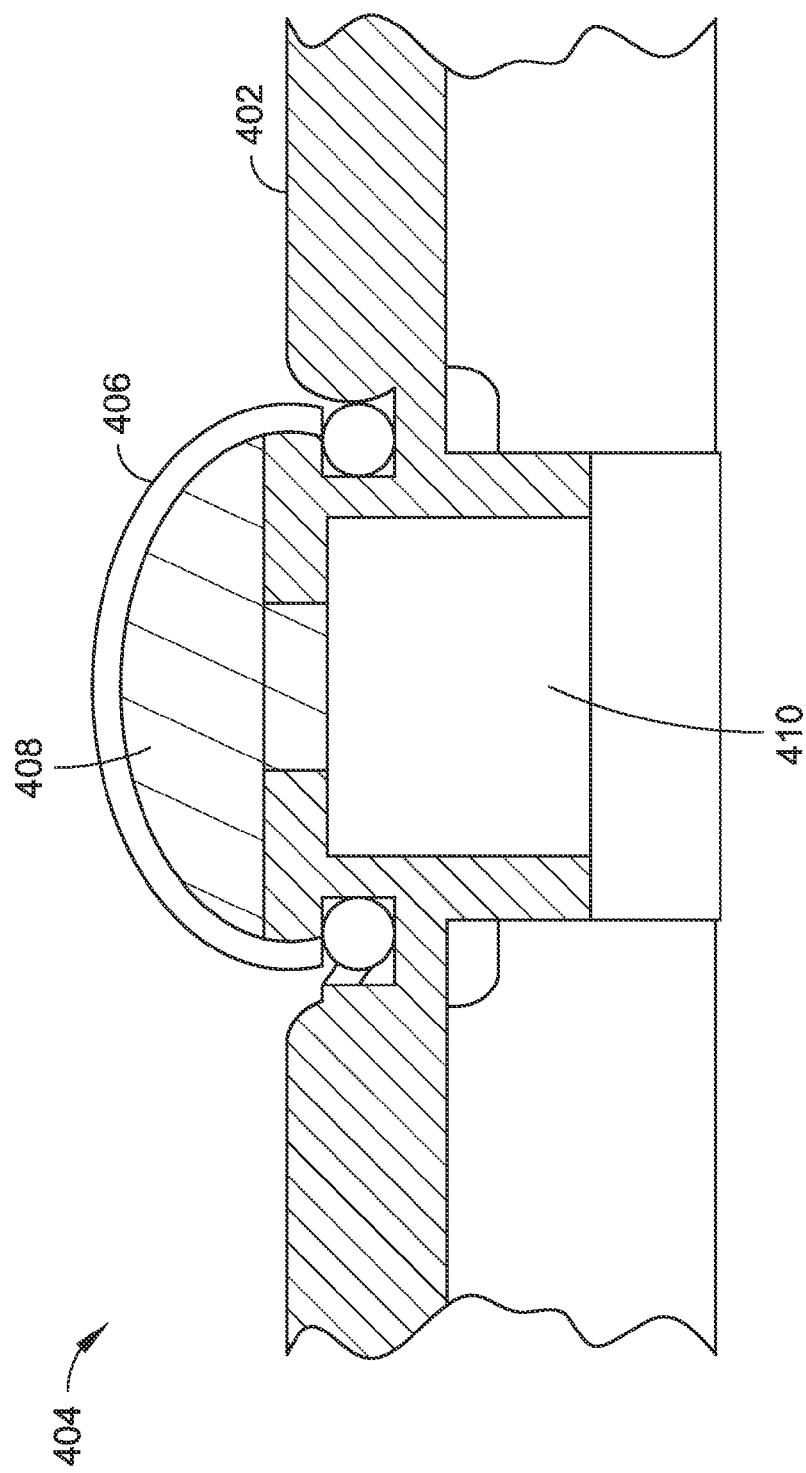

FIG. 11 is a schematic view of a pressure sensor of a gastrointestinal pressure sensing device, in accordance with an embodiment of the present disclosure.

Figure 12:
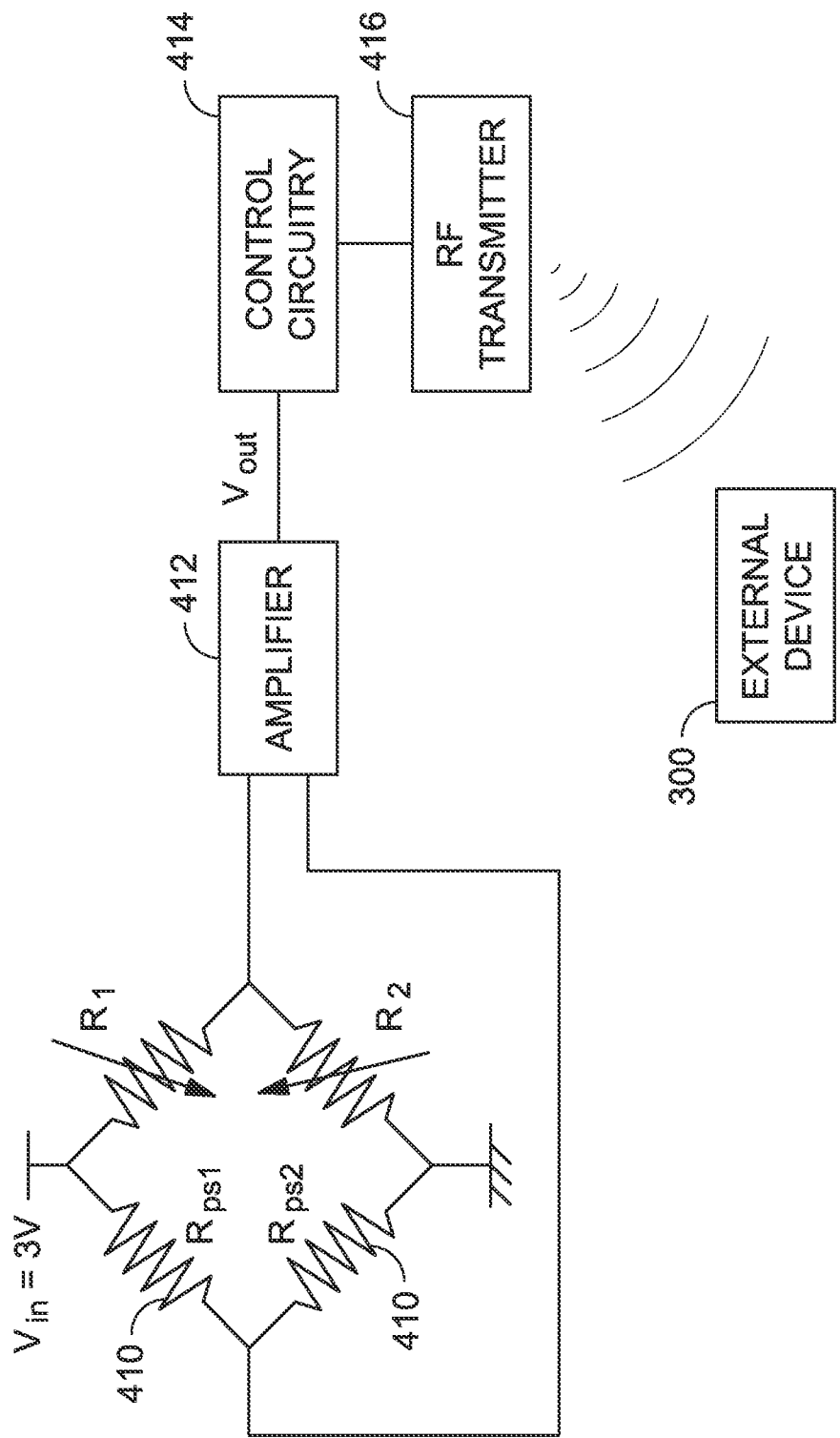

FIG. 12 is a schematic view of a control circuit for detecting ambient and peristaltic gastrointestinal pressure, in accordance with an embodiment of the present disclosure.

FIG. 13A is a schematic view of a gastrointestinal pressure sensing device traveling within a gastrointestinal lumen, in accordance with an embodiment of the present disclosure.

FIG. 13B is a schematic view of a gastrointestinal pressure sensing device traveling within a gastrointestinal lumen, in accordance with an embodiment of the present disclosure.

FIG. 13C is a schematic view of a gastrointestinal pressure sensing device traveling within a gastrointestinal lumen, in accordance with an embodiment of the present disclosure.

Figure 14:
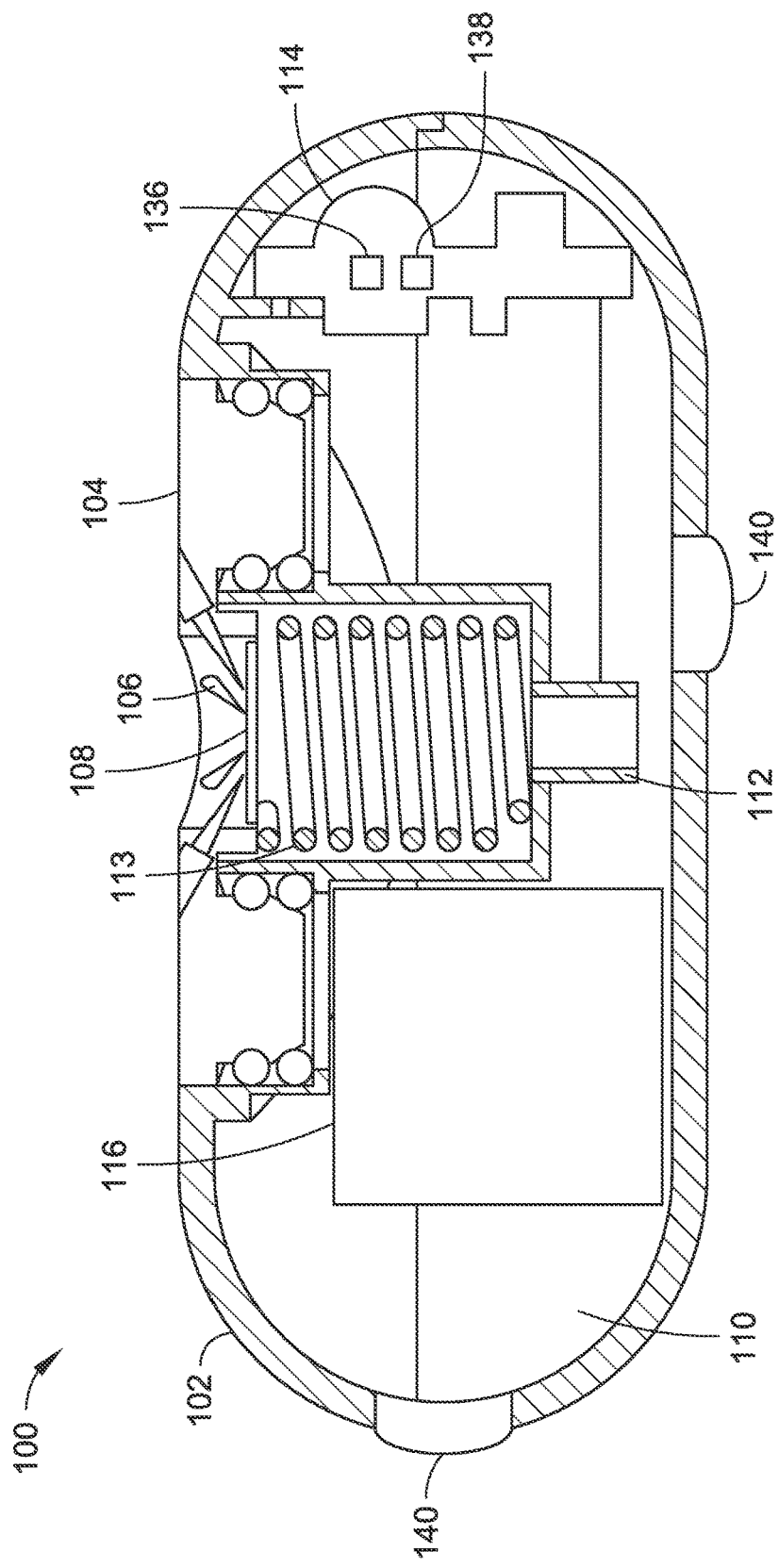

FIG. 14 is a schematic view of a sensor deployment device, in accordance with an embodiment of the present disclosure.

Figure 1:
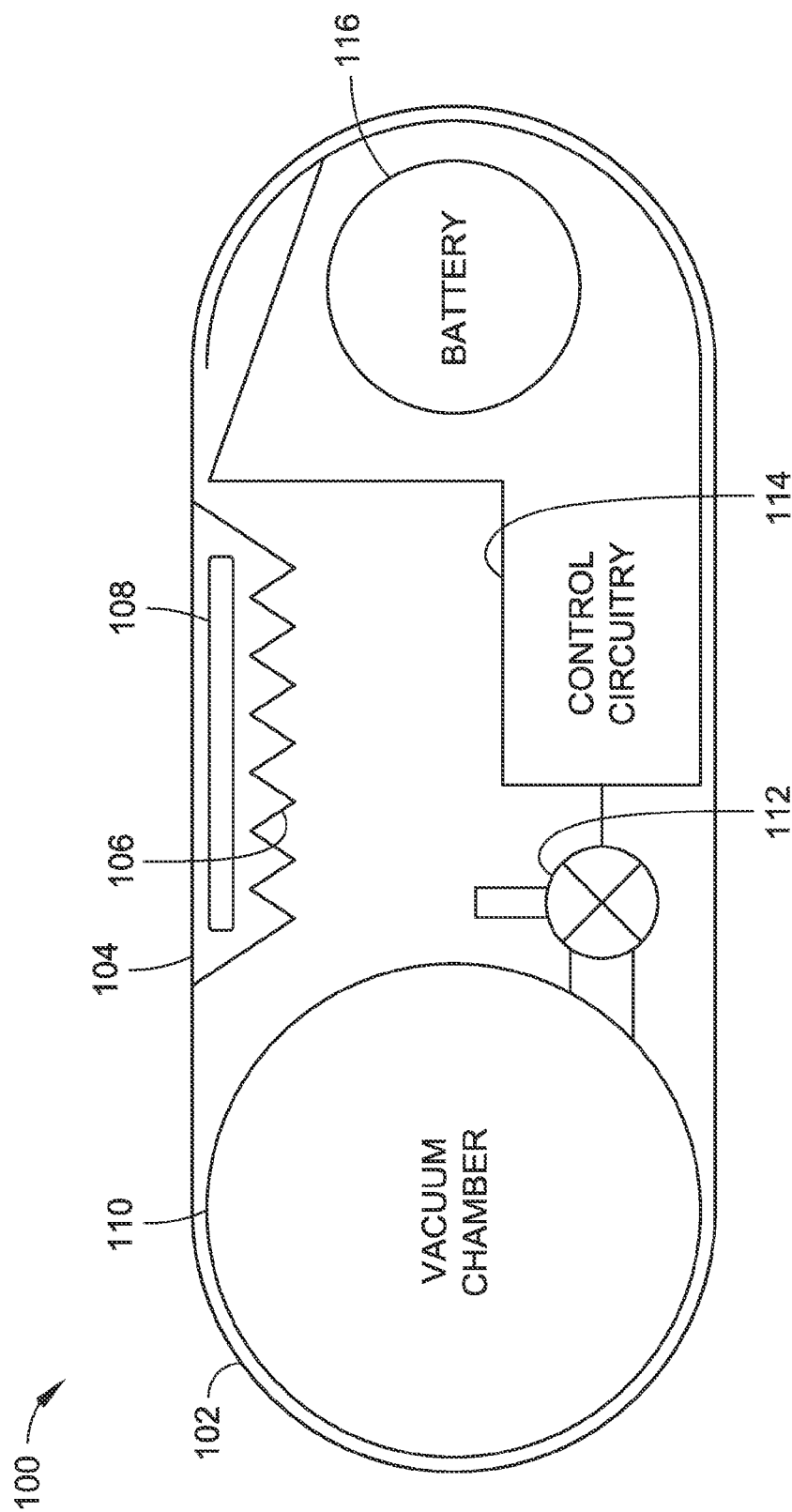
FIG. 1 is a schematic view of a sensor deployment device, in accordance with an embodiment of the present disclosure.
Figure 2:
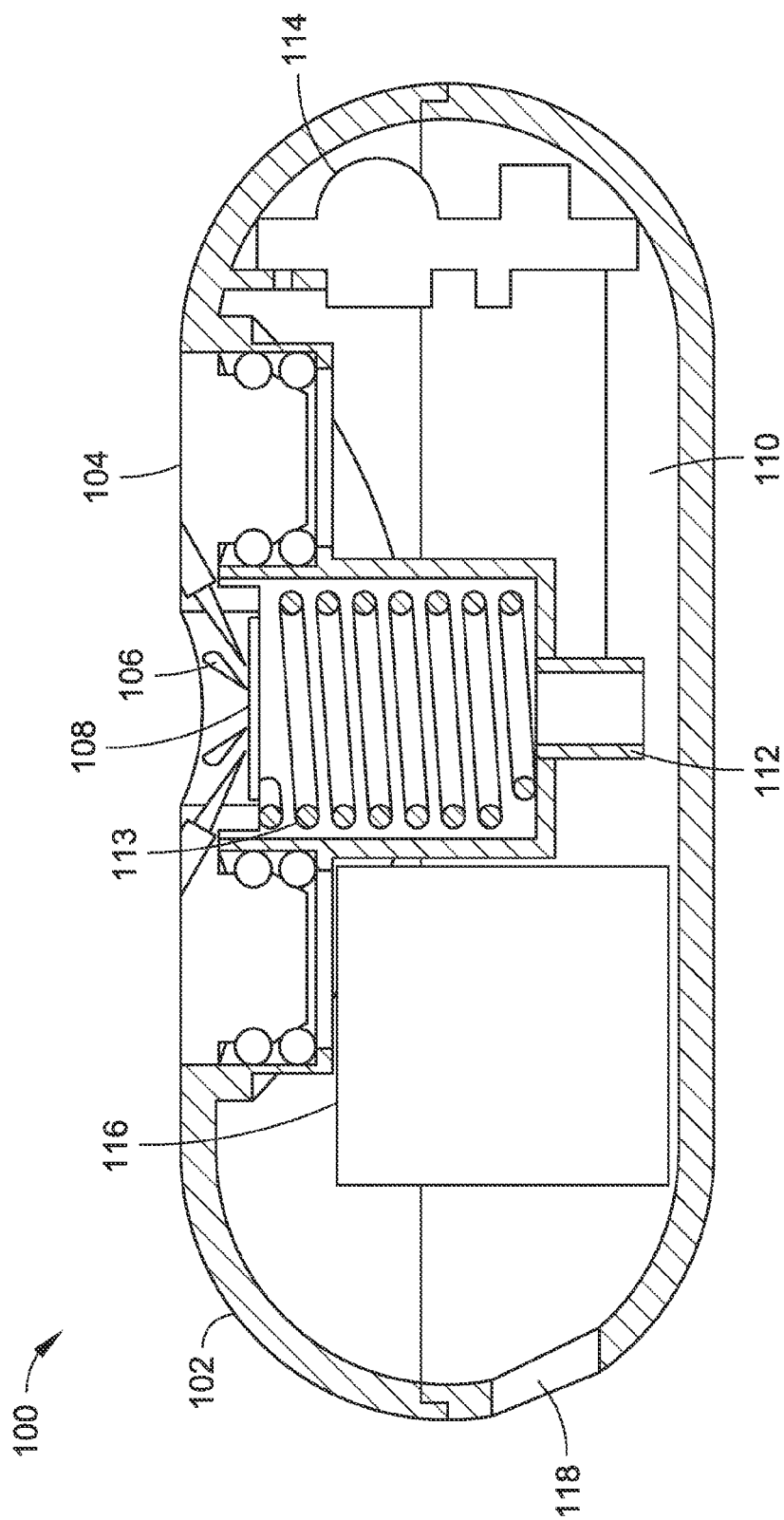
FIG. 2 is a schematic view of a sensor deployment device, in accordance with an embodiment of the present disclosure.
Figure 15:
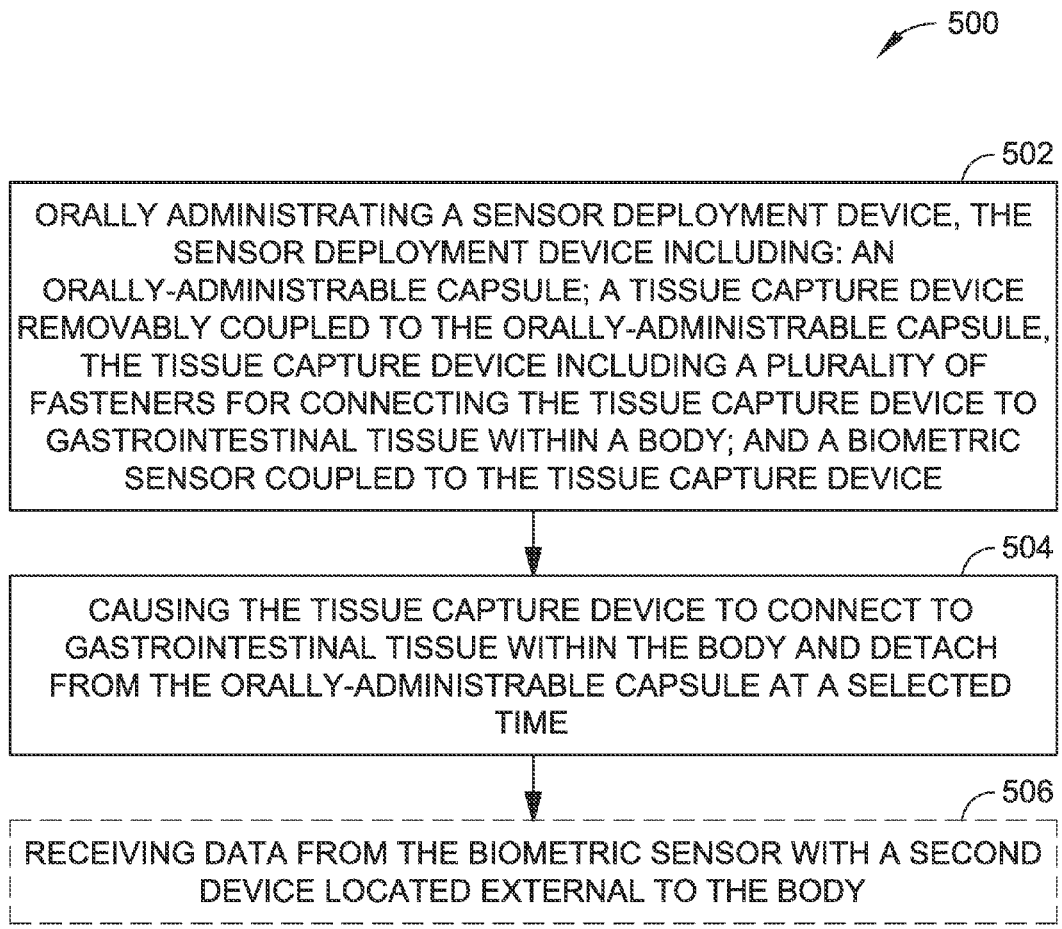

FIG. 15 is a flow diagram illustrating an example process for deploying a sensor within a gastrointestinal lumen of a body, in accordance with an embodiment of a sensor deployment device such as the sensor deployment device shown in FIG. 1 and FIG. 2.

Figure 16:
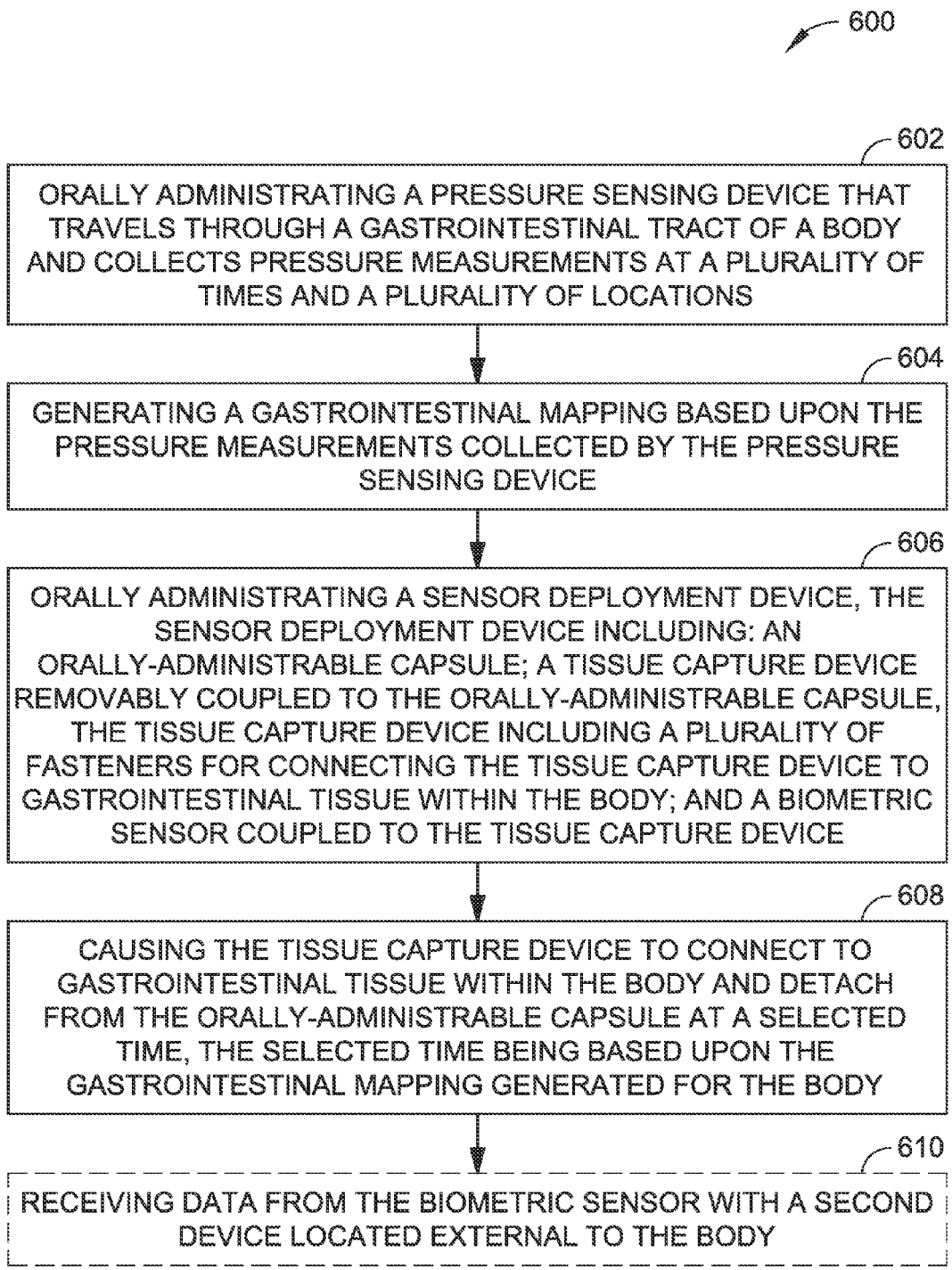

FIG. 16 is a flow diagram illustrating an example process for deploying a sensor within a gastrointestinal lumen of a body, in accordance with an embodiment of a sensor deployment device such as the sensor deployment device shown in FIG. 1 and FIG. 2.

DETAILED DESCRIPTION

Overview

Capsule Endoscopy (CE) has been used in medical diagnosis of intestinal diseases such as obscure gastrointestinal bleeding (OGIB). Several kinds of biometric sensors have been developed to detect bio-data such as pH, blood glucose, partial pressure of carbon oxide and temperature etc. in the esophagus and Gastrointestinal (GI) tract. These bio-data are important for diagnosing gastric motility disorder, upper GI bleeding, gastro esophagus bleeding, diabetes, and so forth. However, CE technology is limited by the lack of long-term sensor deployment solutions. Most CE sensors are passive devices that move through the GI tract by peristalsis and are typically cycled out of a subject's body within a day and may only be present in an area of interest (i.e., a particular portion of the GI tract) for several hours at most. There is a need for CE devices that are suitable for long-term (e.g., several days or weeks long) sensor deployment.

Devices, systems, and methods are disclosed below for long-term GI monitoring. These devices, systems, and methods can be useful in high-risk patients or those with recurring afflictions. In implementations, a biometric sensor is configured for implantation within a GI tract of a body to monitor several data related with diseases mentioned above such as ambient or peristaltic pressure, pH, temperature, an attribute of one or more analytes (e.g., white blood cell count, blood glucose, etc.), or any other bio-data. As described in further detail below, a biometric sensor can be deployed to a location within the GI tract via an MRC and attached to GI tissue utilizing a tissue capture device that can be controllably activated and ejected from the MRC. The biometric sensor can then collect bio-data and transmit the collected data to an externally located device, such as a personal computer, smartphone, tablet, notebook, smartwatch, external monitoring device, or the like. This data can be directly or indirectly (e.g., via a network) made available for health service providers.

Biomimicry has been investigated as a solution for long-term attachment of sensors deployed via orally-administrable micro-robotic capsules (MRCs). For example, MRCs designed for sensor deployment are discussed in Tsubaki, A. T., Lewis, W. M., Terry, B. S. (2014). Implantation and Carrier Mechanism for Long-Term Biosensing in the Small Intestine. *J. Med. Devices,* 8(3), 030956-030956-2 and Yang, X. and Terry, B. S. (2013). An Anchoring Mechanism Used to Implant a Biosensor in the Small Intestine. *Proc. ASME.* 55607, Volume 1A, which are hereby incorporated by reference in their entirety. Through research, it has been found that many species of animals and parasites are successful in attaching to surfaces similar to the lining of the GI tract for long periods of time. Most of these creatures, such as the leech, lampreys, and tapeworm, have a similar mouth structure: a combination of hooks and a sucker, that work together to achieve the attachment function. A bio-inspired replication of this kind of mouth structure is found in the tissue capture device of the sensor deployment device described below.

Example Implementations

FIGS. 1 through 7 illustrate various embodiments of an orally administrable sensor deployment device 100. As shown in FIG. 1, the sensor deployment device 100 includes an orally-administrable capsule 102 (sometimes referred to herein as an "MRC") with a tissue capture device 104 removably coupled to the orally-administrable capsule 102. For example, the tissue capture device 104 can be configured to disengage from the orally-administrable capsule 102 after or substantially at the same time as the tissue capture device 104 is attached to GI tissue at a selected attachment site or region within a GI tract of a body.

Figure 3A:
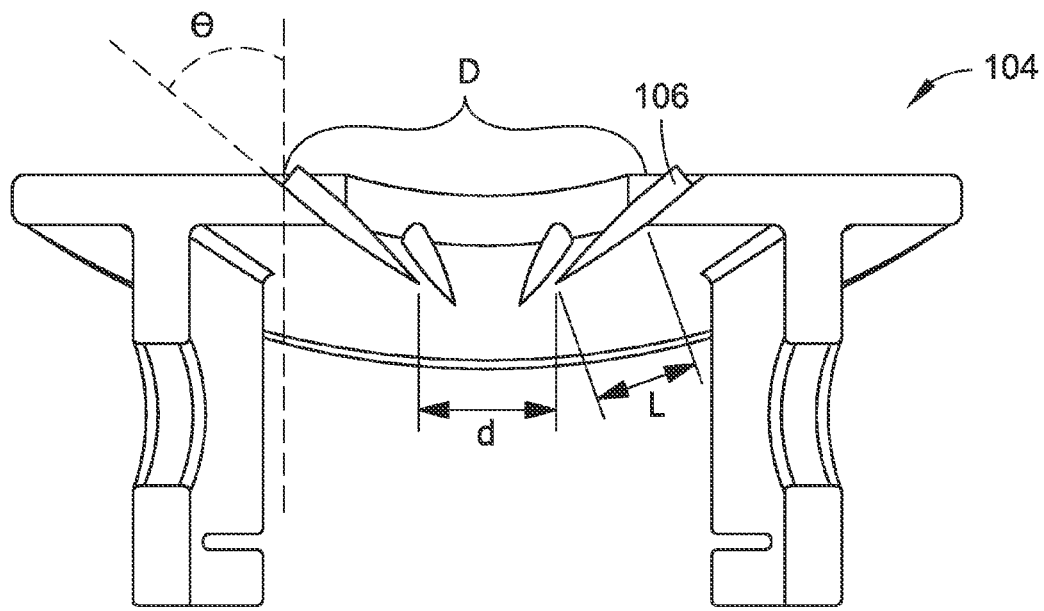
FIG. 3A is a cross-sectional side view of a tissue capture device, in accordance with an embodiment of the present disclosure.
Figure 3B:
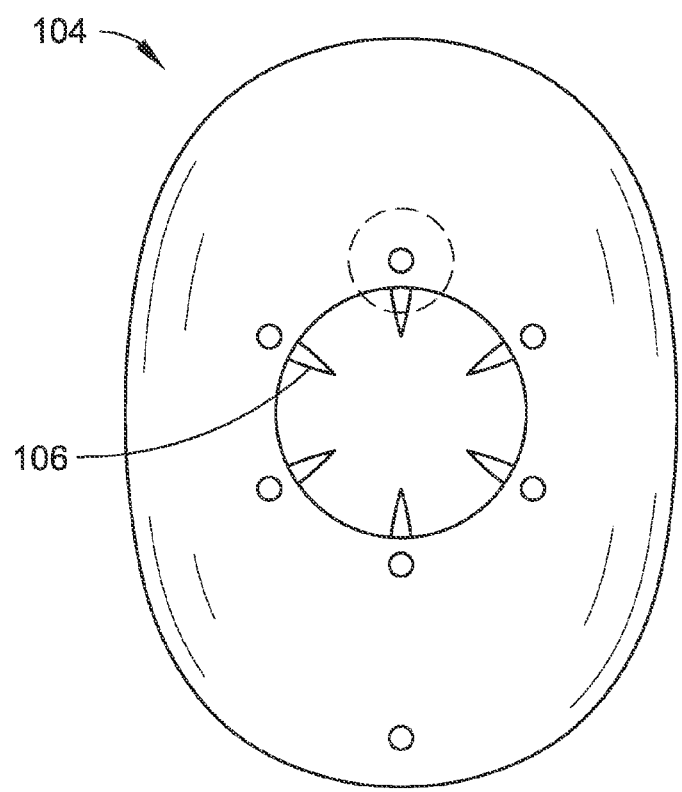
FIG. 3B is a top view of a tissue capture device, in accordance with an embodiment of the present disclosure.

In embodiments, the tissue capture device 104 includes a plurality of fasteners 106 (e.g., micro-needles) for connecting the tissue capture device 104 to GI tissue. A biometric sensor 108 may be coupled to or integrated with the tissue capture device 104 for long term (e.g., several days or weeks long) implantation within the GI tract of the body at the attachment site of the tissue capture device 104. For example, the biometric sensor 108 may include a thermal sensor, a pH sensor, a pressure sensor, an analyte sensor, or any other deployable, in vivo detector or sensor. FIGS. 3A and 3B show a cross-sectional view and a top view of the tissue capture device 104 in accordance with an embodiment of this disclosure. As can be seen, the tissue capture device 104 can include a plurality of fasteners 106, such as needles, spikes, hooks, tooth-like structures, or the like. In some embodiments, the fasteners 106 are selected with a protruding length (L) that is less than a predetermined or estimated thickness of the GI tissue at the selected attachment site or region of the GI tract. The number of fasteners may be, for example, at least 3, at least 4, at least 5, or at least 6 fasteners to enable sufficient anchoring to the GI tissue without causing damage to the tissue at the attachment site. It has been found that, in some embodiments, 6 fasteners provide sufficient anchoring without any significant damage to the attached tissue. The diameter (D) of a receiving (sucker) portion of the tissue capture device should be selected within a suitable range that is large enough to pull tissue into contact with the fasteners 106 and small enough to enable sufficient suction strength. For example, a diameter (D) within of approximately 3 to 7 mm may be acceptable for some applications. It has also been found that, in some embodiments, a diameter in the range of approximately 4 to 6 mm provides appropriate anchoring for long-term deployment. It has also been found that the fasteners 106 attach more firmly to GI tissue drawn into the tissue capture mechanism 104 when set at certain angles (θ), for example, at angles between 30 and 80 degrees (e.g., θ=45° or 60°).

The sensor deployment device 100 may further include a chamber 110 (e.g., a vacuum chamber) within the orally-administrable capsule 102. The chamber 110 may be vacuum sealed with an internal pressure less than an ambient pressure of the orally administrable capsule 102. Accordingly, the chamber 110 can facilitate attachment of the tissue capture device to the GI tissue by drawing the GI tissue towards the plurality of fasteners 106 when a fluid pressure of the chamber 110 is increased (e.g., by breaking the vacuum seal). In embodiments, an actuator 112, such as an electromechanically controlled valve or the like, is configured to cause an increase of the fluid pressure of the chamber 110 (e.g., by letting fluid into the chamber 110) when triggered by control circuitry 114 coupled to the actuator 112. The control circuitry 114 can be powered by a battery 116, also located within the orally administrable capsule 102, or in some embodiments, by a power generator that is driven by peristaltic forces. The control circuitry 114 can be configured to trigger the actuator at a selected time, such as a predetermined time that is input by a user prior to administering the sensor deployment device 100 and/or calculated based upon a determined or estimated location of the sensor deployment device 100 within the GI tract. For example, the control circuitry 114 can be configured to trigger the actuator 112 at a predetermined time associated with the orally-administrable capsule 102 reaching a particular location within the GI tract, such as the small intestine or a particular portion thereof. In some embodiments, the predetermined time is based upon a GI mapping generated utilizing pressure measurements taken at a plurality of times and locations within the GI tract. For example, a mapping can be created using an orally-administrable pressure sensing device, such as device 400 described below. In other embodiments, an external suction pressure can be applied at a selected time to a chamber 110 within the orally administrable capsule via a suction port 118 (shown in FIG. 2), having substantially the same effect of drawing GI tissue towards the fasteners 106 of the tissue capture device 104.

As illustrated in FIG. 2, the sensor deployment device 100 can further include a compressed spring 113 or other ejector configured to push the tissue capture device 104 from the orally administrable capsule 102 when the tissue capture device 104 is attached to GI tissue. The tissue capture device 104 may be couple into snug fittings of the orally administrable capsule 102. In some embodiments, O-rings or rubber washers may be used to create a snug interface between the capsule fittings and interfacing portions of the tissue capture device 104. The interface should hold the tissue capture device 104 and the orally administrable capsule 102 together tightly until the tissue capture device 104 is ejected from the orally administrable capsule 102. In some embodiments, rather than being forcefully ejected, the orally administrable capsule 102 may simply be pulled away from the tissue capture device 104 by peristaltic forces after the tissue capture device 104 has been attached to GI tissue.

FIGS. 4A through 4C illustrate an embodiment of the sensor deployment device 100 traveling through a GI tract 202 of a body 200. FIG. 4A illustrates the sensor deployment device 100, fully intact, traveling through a lumen of the GI tract 202. The sensor deployment device 100 is configured to travel passively through the GI tract 202 via peristaltic forces. As discussed above, the control circuitry 114 can be configured to trigger an actuator 112 to cause fluid flow into the chamber 110 located inside the orally administrable capsule 102. FIG. 4B shows how, as a result of the fluid flow into the chamber 110, GI tissue 204 is drawn towards the fasteners 106 of the tissue capture device 104. The tissue capture device 104 is then attached to a luminal wall of the GI tract 202, and the remainder of the orally administrable capsule 102 disengages from the tissue capture device 104 and is eventually removed from the body 200 by peristaltic forces. The biometric sensor 108 is thus implanted within the GI tract 202 until the connection between the tissue capture device 104 and the GI tissue 204 wears away due to continued cell growth and peristalsis. Using the tissue capture device 104 to implant the biometric sensor 108 may enable multiple day and possibly multiple week long sensing periods at selectable sites within the GI tract 202; whereas, most sensors deployed via MRCs are only capable of collecting data as they travel through the GI tract.

Embodiments of the control circuitry 114 are illustrated in FIGS. 5A and 5B. As shown in FIG. 5A, the control circuitry 114 can include a processor 120 (e.g., microprocessor or microcontroller) configured to execute program instructions 124 from a communicatively coupled storage medium 122 (e.g., solid-state memory device). As shown in FIG. 5B, the control circuitry 114 can also include a simple timer circuit 126 comprised of discrete components, an ASIC, an FPGA, a PIC, or the like. The control circuitry 114 can be programmed or otherwise configured to trigger the actuator 112 after a predetermined time from oral administration (or activation just prior to being administered). The predetermined time can be input by a user (e.g., a health care provider) and/or calculated based upon one or more attributes of a subject being treated. In some embodiments, the predetermined time can be based upon a GI mapping specific to the subject's body 200. For example, the predetermined time may be based upon a predetermined or estimated time required for the sensor deployment device 100 to reach a selected attachment site within the GI tract 202 of the body 200.

Another embodiment is illustrated in FIG. 6, where the control circuitry 114 is be coupled with a receiver 128 (e.g., RF receiver, Bluetooth receiver, or the like) for receiving wireless communications from a second device 300 located external to the body 200. In some embodiments, the control circuitry 114 may be configured to receive program instructions (e.g., timer configurations) or commands (e.g., commands for triggering the actuator 112) from the second device 300. Examples of the second device 300 can include a personal computer, notebook, tablet, a smartphone, smartwatch, or the like. In some embodiments, control circuitry 114 may be further configured to communicate data (e.g., via an RF transmitter) to the second device 300. For example, the control circuitry 114 may communicate location data or biometric data collected from other sensors within the sensor deployment device 100. In some embodiments, the control circuitry 114 may receive program instructions or commands from the second device 300 based upon data communicated to the second device 300. For example, the second device 300 may send a command for triggering the actuator 112 in response to receiving data indicating that the sensor deployment device 100 may have reached the selected attachment site or in response to receiving biometric data that suggests further monitoring would be beneficial at a location of the sensor deployment device 100.

Figure 7:
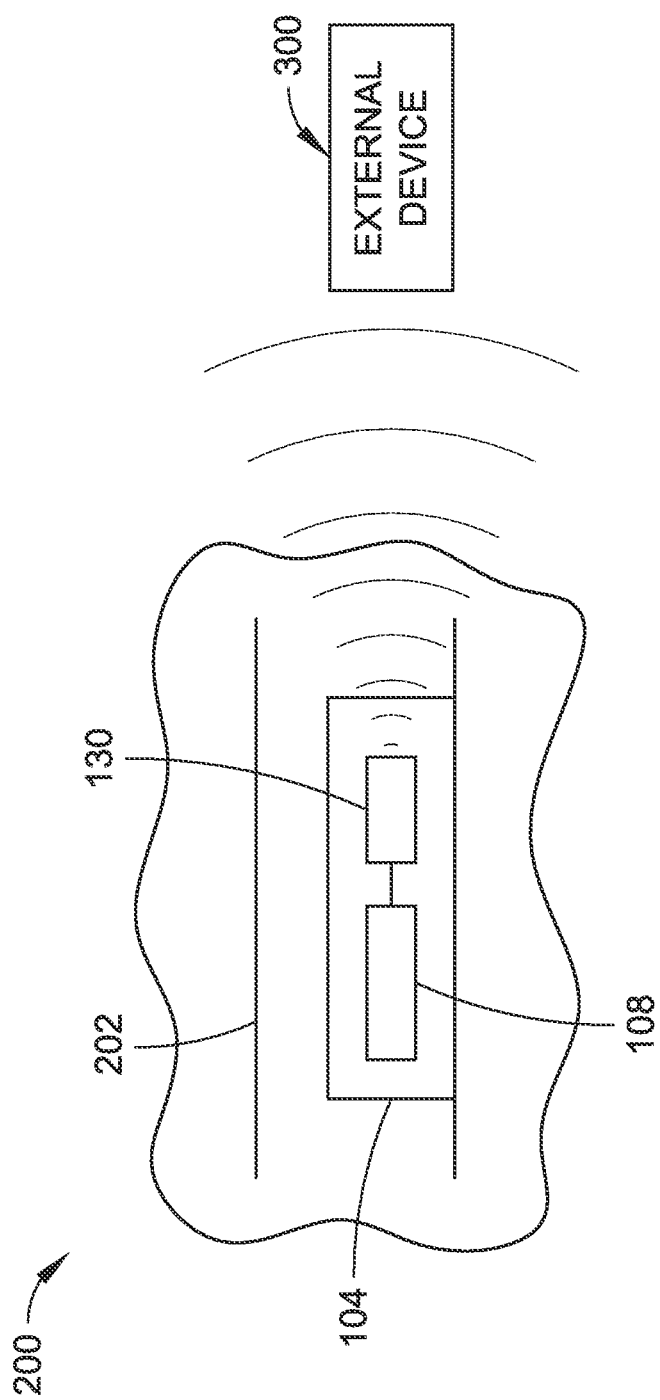
FIG. 7 is a schematic view of a sensor implanted within a gastrointestinal lumen of a body in wireless communication with a second device external to the body, in accordance with an embodiment of the present disclosure.

As shown in FIG. 7, once the tissue capture device 104 is implanted within the body 200 by attachment of the tissue capture device 104 to a luminal wall of the GI tract 202, the biometric sensor 108 can collect data (e.g., pressure measurements, temperature, pH, presence/absence or other attributes for one or more analytes, etc.). For example, the biometric sensor 108 may collect data continuously, periodically, or in response to one or more requests received from an external device 300. A transmitter 130 (e.g., RF transmitter) coupled to the biometric sensor 108 may facilitate communication of the sensor data to the external device 300. In some embodiments, the biometric sensor 108 can also be coupled to a receiver (e.g., RF receiver) for receiving program instructions or commands (e.g., data requests) from the external device 300.

Many different kinds of biometric sensors 108 can be deployed via the sensor deployment device 100 for various health monitoring applications. Some health monitoring applications are concerned with continuous or periodic detection for risk indicators (e.g., GI bleeding, temperature or pH inconsistency, pressure changes, etc.). However, other applications can include GI monitoring for general health applications, such as weight management. In some embodiments, for example, the biometric sensor 108 can include a flow sensor configured to detect a volumetric flow rate at the attachment site within the GI tract (e.g., flow rate through the small intestine). The volumetric flow rate can be monitored with data (e.g., user-input data) about food intake to characterize a subject's metabolic profile and provide individualized dietary recommendations (e.g., quantity and/or quality of food recommendations, a measure of "fullness," etc.). This information can be used for long term weight loss assistance and may be helpful in identifying behavioral defects. For example, individuals that continue to consume food after reaching a generally accepted level of "fullness" may suffer from certain eating disorders that require psychiatric intervention. The foregoing example illustrates one possible application of long-term GI sensor deployment. Those skilled in the art will further appreciate that the sensor deployment device 100 has utility in many other applications where long-term GI monitoring is required or helpful.

Figure 8:
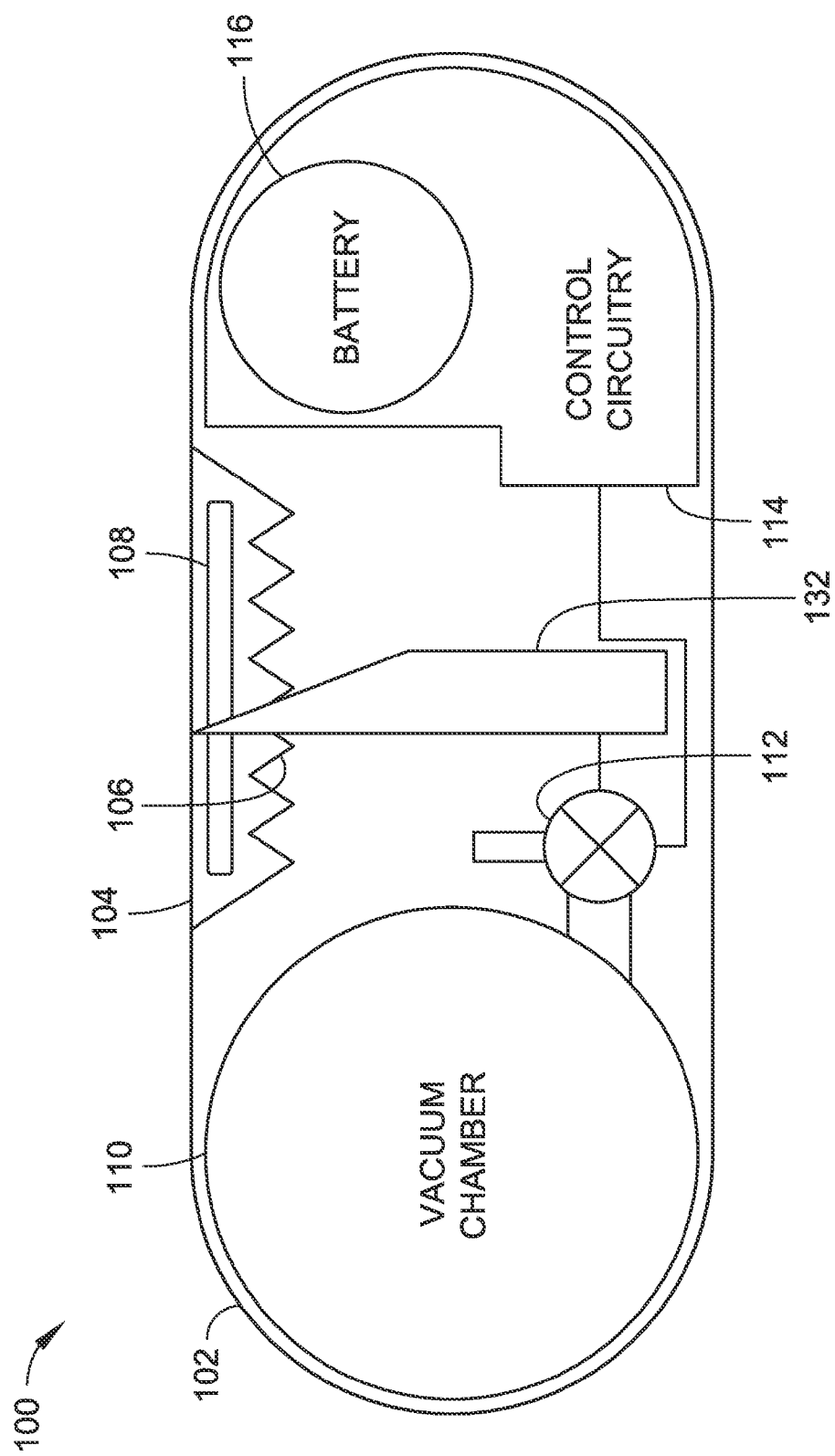
FIG. 8 is a schematic view of an orally-administrable deployment device for implanting sustained release drugs (SRDs) in the intraperitoneal space, in accordance with an embodiment of the present disclosure.

Looking now to FIG. 8, another embodiment of the deployment device 100 is shown for deployment of a sustained release drug (SRD) 134 instead of or in addition to the biometric sensor 108. In some embodiments, the deployment device 100 may include a catheter 132 located within the orally administrable capsule 102. The catheter 132 may be configured to puncture the luminal wall of the GI tract 202 upon attachment of the tissue capture device 104 to facilitate deployment of the SRD 134 within the intraperitoneal space of the body 200. For example, FIG. 9A shows the catheter puncturing a portion of GI tissue that is drawn into the tissue capture device 104 towards the fasteners 106. Upon puncturing the GI tissue, the catheter 132 may be configured to release the SRD 134 into the intraperitoneal space of the body 200. The tissue capture device 104 can include a suture mechanism (e.g., bio-compatible adhesive or staples) to close the incision made by the catheter 132 or may simply be configured to apply pressure at the attachment site to close the incision until the GI tissue sufficiently heals. For example, FIG. 9B shows the tissue capture device 104 closing the incision made by the catheter 132 after the SRD 134 has been deployed within the intraperitoneal space.

As mentioned above, the timing for attachment of the tissue capture device 104 and corresponding deployment of the biometric sensor 108 and/or SRD 134 may be controlled in accordance with a predetermined GI mapping of the body 200. For example, the control circuitry 114 can be configured to trigger the actuator 112 for attachment of the tissue capture device 104 to the luminal wall of the GI tract 202 based upon an expected position of the sensor deployment device 100 within the GI tract 202. Because each body has a somewhat unique peristalsis cycle, a body-specific GI mapping can assist in optimizing deployment timing and thus being able to effectively deploy the tissue capture device 104 at an attachment site suitable for long-term anchoring, biometric measurements, and/or SRD deployment. To facilitate a body-specific GI mapping, another MRC can be used in a two-pill GI mapping and deployment system.

An embodiment of an orally administrable pressure sensing device 400 is shown in FIG. 10. The pressure sensing device 400 can be used to collect ambient and peristaltic pressures at a plurality of times and locations throughout the GI tract 202 of a body 200. Using the pressure data collected over time that the pressure sensing device 400 travels through the body, an expected, baseline model (e.g., nominal GI map) can be modified to generate a GI mapping for the body 200. For example, an average rate of motion can be identified for the body or for particular portions of the GI tract (e.g., rate of motion within the small intestine), detected pressure changes can be used to determine passage of the pressure sensing device 400 from one portion of the GI tract to another (e.g., entering the small intestine), and so forth. As shown in FIG. 10, the pressure sensing device 400 can include an orally administrable capsule 402 with at least two pressure sensors 404 embedded in the surface of the capsule 402. In the embodiment shown in FIG. 10, the pressure sensing device 400 includes at least a first sensor 404 located at an end of the orally administrable capsule 402 and at least a second sensor 404 located at a lateral surface or side portion of the orally administrable capsule 402.

As shown in FIG. 11, each pressure sensor 404 can include a transducer 410 that ultimately receives ambient and/or peristaltic forces and generates a corresponding electrical signal. A variety of designs may be employed to enhance sensitivity of the transducer 410. For example, each pressure sensor 404 can include a button coupled to an aluminum beam that deforms and affects the transducer 410 when pressure is applied to the button. In the embodiment shown in FIG. 11, each pressure sensor 404 includes a rubber sheet 406 formed over the transducer 410 with a silicon oil 408 filling the space in between. Thus, when the rubber sheet 406 is pressed down by ambient or peristaltic forces, the transducer 410 is affected by the resulting deformation of the silicon oil 408 in between the rubber sheet 406 and the transducer 410. Those skilled in the art will appreciate that additional designs may be employed to achieve requisite sensitivity of the pressure sensors 404 for detecting ambient and peristaltic pressures within the GI tract 202 of a body 200.

FIG. 12 shows an embodiment of circuitry within the orally-administrable capsule 402 for processing the pressure sensor 404 outputs and relaying the collected pressure measurements to an external device 300. In some embodiments, the transducer 410 of each pressure sensor 404 is coupled to or comprises a leg of a Wheatstone bridge. Embodiments of pressure sensor circuitry and other design features are described in further detail in Li, P. and Terry, B. S. (2014). Design of a Swallowable Microrobotic Capsule for Measuring Small Intestine Pressure. *J. Med. Devices*, 8(3), 030910-030910-2, which is incorporated herein by reference in its entirety. The pressure detected by each of the sensors 404 affects a resistance value (e.g., $R_{ps1}$ or $R_{ps2}$) of the corresponding leg of the Wheatstone bridge. Typically, peristaltic pressure (i.e., pressure due to the luminal walls pressing on the capsule 402) will be experienced at one of the pressure sensors 404 or at none of them. Some example scenarios are shown in FIGS. 13A through 13C. At narrower luminal passages (e.g., in the small intestine), peristaltic pressure is likely to be detected by the pressure sensor 404 located at the side portion of the capsule 402 (e.g., as shown in FIG. 13A). At wider luminal passages, peristaltic pressure is likely to be detected by the pressure sensor 404 located at the end of the capsule 402 (e.g., as shown in FIG. 13B) or by neither one of the pressure sensors (e.g., as shown in FIG. 13C). The voltage or current detected across two nodes of the Wheatstone bridge can be analyzed to determine which sensor (if any) is detecting the most pressure, the amount of pressure detected, and so forth. In some embodiments, the Wheatstone bridge's nodal outputs are coupled to an amplifier (e.g., an Op-Amp) or other pre-processing front-end circuitry. The output is then fed into a control circuit 414, such as a processor, microcontroller, ASIC, FPGA, or the like, and communicated via a transmitter 416 (e.g., RF transmitter) to an external device 300 that records the measured pressures over time.

The external device 300 can further be configured to adjust a baseline model according to the received measurements. For example, the external device 300 can determine a location of the pressure sensing device 400 within the GI tract 202 of the body 200 with higher accuracy by using the pressure measurements to determine how far from an expected (nominal) location the pressure sensing device 400 is located. Thus, the external device 300 can generate a body-specific model that takes actual peristalsis characteristics of the body into account. In some embodiments, the control circuitry 414 of the pressure sensing device 400 further includes or is coupled to a receiver (e.g., RF receiver). The control circuitry 414 can be further configured to send signals to and/or receive triangulation signals from at least two sources (e.g., external devices 300) having known locations relative to the body 200. Based upon the triangulation signals, the location of the pressure sensing device 400 can also be found. Triangulation can be useful, for example, when the pressure sensors 404 become inactive or exhibit unusual readings. In such cases, it can be useful to know whether the pressure sensing device 400 has become stuck or defective. Additionally, triangulation can be used to eliminate the need for a baseline model. For example, triangulation-based positioning and pressure measurements collected over time can be used to generate a GI mapping for the body.

In some embodiments, the sensor deployment device 100 may include certain features of the pressure sensing device 400, and vice versa. FIG. 14 shows an embodiment, for example, where the sensor deployment device 100 includes pressure sensors 140 substantially similar or identical to the pressure sensors 404 described above. The control circuitry 114 may be configured to communicate pressures collected at a plurality of locations and times to the external device 300. The control circuitry 114 may receive a command or request from the external device 300 to deploy the tissue capture device 104 when the pressure measurements and timing are consistent with a selected attachment site within the GI tract. Alternatively, the control circuitry 114 of the sensor deployment device 100, on its own, may be configured to determine when it has reached an appropriate attachment site within the GI tract based upon time and pressure data. For example, the actuator 112 may be triggered to deploy the tissue capture device 104 after a predetermined time period, only when a certain pressure threshold or range is reached.

In some embodiments, the sensor deployment device 100 may include additional location, orientation, or motion sensors to assist with location determination of the sensor deployment device 100 within the GI tract. For example, the sensor deployment device 100 can further include an inertial measurement unit, such as a multiple-axis (e.g., three-axis) accelerometer 136 and/or a gyroscope 138, coupled to the control circuitry 114 or a pH sensor. Inertial data, pH measurements, and/or pressure measurements can be used along with timing data to pinpoint the location of the sensor deployment device 100 within the GI tract. The control circuity 114 can use any combination of sensor data along with timing data to determine an appropriate time for deployment of the tissue capture device 104. Additionally, sensor data (e.g., inertial, pH, or pressure data) can be transmitted (e.g., via an RF transmitter) to the external device 300 for external control of the sensor deployment device 100 or simply for additional (non-stationary) monitoring of the GI tract.

Example Processes

FIGS. 15 and 16 illustrate example processes 500 and 600, respectively. Processes 500 and 600 can be manifested by the systems and devices described above (e.g., device 100, device 300, and/or device 400) and can include one or more steps or processing blocks for carrying out one or more of the functions or operations described above. However, processes 500 and 600 are not limited to the system and device embodiments described herein and may alternatively be manifested by any combination of components suitable for carrying out the methodology described below.

A flow diagram in FIG. 15 illustrates a method 500 of deploying a sensor in a GI tract of a body. At step 502, a sensor deployment device (e.g., device 100) is orally administered to a subject. For example, the subject may be directed to swallow an MRC (e.g., capsule 102) including a removable tissue capture device (e.g., device 104) with a biometric sensor (e.g., sensor 108) integrated therewith or coupled thereto and a plurality of fasteners for connecting to GI tissue within the GI tract of the subject's body. At a selected time, the method 500 proceeds to step 504, wherein the tissue capture device is attached to a luminal wall of the GI tract. For example, GI tissue from the luminal wall may be drawn in towards fasteners (e.g., fasteners 106) of the tissue capture device by fluid flow directed into a vacuum chamber (e.g., chamber 110). In some embodiments, fluid may flow into the chamber when the chamber is opened by an actuator (e.g., actuator 112). After or at substantially the same time as the tissue capture device is attached to the GI tissue, the tissue capture device is disengaged from the MRC. The MRC continues to move through the body while the tissue capture device remains implanted at the attachment site of the GI tract. At step 506, data can be received from the biometric sensor at a second device (e.g., device 300) located outside of the body. For example, the biometric sensor can transmit data to the second device continuously, periodically, according to a predetermined schedule, when a biometric threshold (e.g., threshold temperature) is breached, or in response to a command or request received from the second (externally located) device. Biometric data can be collected until the tissue capture device detaches from the luminal wall of the GI tract, perhaps days or possibly weeks later, due to cellular growth and/or peristalsis.

FIG. 16 shows another flow diagram illustrating a method 600 of generating a GI mapping for a body and deploying a sensor in a GI tract of the body. At step 602, a pressure sensing device (e.g., device 400) is orally administered to a subject. For example, the subject may be directed to swallow an MRC (e.g., capsule 402) including one or more pressure sensors 404. The pressure sensing device may passively travel through the GI tract of the subject's body and collect pressure measurements at a plurality of locations and times. For example, the pressure sensing device may collect pressure measurements substantially continuously, periodically, or according to a schedule. The pressure sensing device may communicate the collected pressure measurements to a second device (e.g., device 300) located outside of the body. At step 604, a GI mapping can be generated with the collected pressure measurements. For example, a model of expected MRC locations within the GI tract at certain times can be adjusted according to the pressure measurements.

Because certain pressure levels or changes can indicate that the MRC has entered or left certain portions of the GI tract, the measurements can be used to pinpoint the actual location of the MRC and the model can be adjusted to compensate from a deviation between the actual location and the expected location of the MRC. In some embodiments, triangulation data can also be used to determine a location of the MRC. After a GI mapping has been generated, the method 600 can proceed to step 606, where a sensor deployment device (e.g., device 100) is orally administered to the subject. At a selected time, the method 600 proceeds to step 604, wherein a tissue capture device (e.g., device 104) carried by the sensor deployment device is attached to a luminal wall of the GI tract. The selected time may be based upon the GI mapping generated with the orally administered pressure sensing device. For example, the selected time may be associated with a predetermined period of time required for an MRC (e.g., device 100 or device 400) to reach a particular site within the GI tract (e.g., the small intestine or a particular portion thereof). After or at substantially the same time as the tissue capture device is attached to the GI tissue, the tissue capture device is disengaged from the remainder of the sensor deployment MRC. The remainder of the MRC continues to move through the body while the tissue capture device remains implanted at the attachment site of the GI tract. At step 606, data can be received from the biometric sensor at a second device (e.g., device 300) located outside of the body. For example, the biometric sensor can transmit data to the second device continuously, periodically, according to a predetermined schedule, when a biometric threshold (e.g., threshold temperature) is breached, or in response to a command or request received from the second (externally located) device. Biometric data can be collected until the tissue capture device detaches from the luminal wall of the GI tract, perhaps days, weeks, or possibly months later, due to cellular growth and/or peristalsis.

It should be recognized that the various functions, operations, blocks, or steps described throughout the present disclosure may be carried out by any combination of hardware, software, or firmware. In some embodiments, various steps or functions are carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, mainframe computing system, workstation, image computer, parallel processor, or any other device known in the art. In general, the terms "controller" and "computing system" are broadly defined to encompass any device having one or more processors, which execute instructions from a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

It is further contemplated that any embodiment of the disclosure manifested above as a system or method may include at least a portion of any other embodiment described herein. Those having skill in the art will appreciate that there are various embodiments by which systems and methods described herein can be implemented, and that the implementation will vary with the context in which an embodiment of the disclosure is deployed.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. A sensor deployment device, comprising:
   an orally-administrable capsule;
   a tissue capture device removably coupled to the orally-administrable capsule, the tissue capture device including a plurality of fasteners for connecting the tissue capture device to gastrointestinal tissue within a gastrointestinal tract of a body;
   a biometric sensor coupled to the tissue capture device;
   a chamber within the orally-administrable capsule, the chamber being configured to draw gastrointestinal tissue towards the plurality of fasteners when a fluid pressure of the chamber is increased;
   an actuator configured to cause an increase of the fluid pressure of the chamber; and
   control circuitry coupled to the actuator, the control circuitry being configured to trigger the actuator to cause the increase of the fluid pressure of the chamber at a selected time,
   wherein the tissue capture device is configured to detach from the orally-administrable capsule, and
   wherein the biometric sensor remains coupled to the tissue capture device after the tissue capture device detaches from the orally-administrable capsule.

2. The sensor deployment device of claim 1, wherein the control circuitry includes a processor in communication with a storage medium, the storage medium bearing program instructions that are executable by the processor.

3. The sensor deployment device of claim 1, wherein the control circuitry includes a timer circuit.

4. The sensor deployment device of claim 1, wherein the selected time is based upon a gastrointestinal mapping.

5. The sensor deployment device of claim 4, wherein the gastrointestinal mapping is derived from pressure data collected by a second orally-administrable capsule at a plurality of times and a plurality of locations within the gastrointestinal tract of the body.

6. The sensor deployment device of claim 1, further comprising:
   a radio frequency (RF) receiver coupled with the control circuitry, wherein the selected time for triggering the actuator is based upon a communication received, via the RF receiver, from a second device located external to the body.

7. The sensor deployment device of claim 1, further comprising:
   a radio frequency (RF) transmitter coupled with the biometric sensor, the RF transmitter being configured to communicate data from the biometric sensor to a second device located external to the body.

8. The sensor deployment device of claim 1, wherein each fastener of the plurality of fasteners is disposed at an angle ranging between thirty degrees and eighty degrees with respect to an axis that is perpendicular to a top surface of the tissue capture device.

9. A sensor deployment device, comprising:
an orally-administrable capsule;
a tissue capture device removably coupled to the orally-administrable capsule, the tissue capture device including a plurality of fasteners for connecting the tissue capture device to gastrointestinal tissue within a body;
a biometric sensor coupled to the tissue capture device;
a chamber within the orally-administrable capsule, the chamber being configured to draw gastrointestinal tissue towards the plurality of fasteners when a fluid pressure of the chamber is increased;
an actuator configured to cause an increase of the fluid pressure of the chamber; and
control circuitry coupled to the actuator, the control circuitry being configured to trigger the actuator to cause the increase of the fluid pressure of the chamber at a selected time, the selected time being based upon a gastrointestinal mapping derived from pressure data collected by a second orally-administrable capsule at a plurality of times and a plurality of locations within a gastrointestinal tract of the body,
wherein the biometric sensor remains coupled to the tissue capture device after the tissue capture device detaches from the orally-administrable capsule.

10. The sensor deployment device of claim 9, wherein the control circuitry includes a processor in communication with a storage medium, the storage medium bearing program instructions that are executable by the processor.

11. The sensor deployment device of claim 9, wherein the control circuitry includes a timer circuit.

12. The sensor deployment device of claim 9, further comprising:
a radio frequency (RF) transmitter coupled with the biometric sensor, the RF transmitter being configured to communicate data from the biometric sensor to a second device located external to the body.

13. The sensor deployment device of claim 9, wherein the collected pressure data includes ambient pressure measurements.

14. A sensor deployment method, comprising:
orally administrating a sensor deployment device, the sensor deployment device including:
an orally-administrable capsule;
a tissue capture device removably coupled to the orally-administrable capsule, the tissue capture device including a plurality of fasteners for connecting the tissue capture device to gastrointestinal tissue within a body; and
a biometric sensor coupled to the tissue capture device; and
causing the tissue capture device to, at a selected time, connect to gastrointestinal tissue within a gastrointestinal tract of the body,
wherein the tissue capture device is configured to detach from the orally-administrable capsule, and
wherein the biometric sensor remains coupled to the tissue capture device after the tissue capture device detaches from the orally-administrable capsule.

15. The sensor deployment method of claim 14, wherein the selected time is based upon a predetermined time interval.

16. The sensor deployment method of claim 15, wherein the predetermined time interval is based upon a gastrointestinal mapping.

17. The sensor deployment method of claim 16, wherein the gastrointestinal mapping is derived from pressure data collected by a second orally-administrable capsule at a plurality of times and a plurality of locations within the gastrointestinal tract of the body.

18. The sensor deployment method of claim 14, further comprising:
receiving data from the biometric sensor with a second device located external to the body.

19. The sensor deployment method of claim 18, wherein the data received from the biometric sensor includes at least one of a detected pressure, a detected pH, a detected temperature, or a detected attribute of an analyte.

20. The sensor deployment method of claim 14, wherein causing the tissue capture device to connect to gastrointestinal tissue within the body comprises:
causing fluid to flow into a chamber positioned relative to the tissue capture device such that the gastrointestinal tissue is drawn towards the fasteners of the tissue capture device.

* * * * *